(12) United States Patent
Alabata et al.

(10) Patent No.: US 9,248,167 B2
(45) Date of Patent: Feb. 2, 2016

(54) EXFOLIATIVE HAIR RETENTION-PROMOTING FORMULATION

(71) Applicant: Restorsea, LLC, New York, NY (US)

(72) Inventors: Enrique P. Alabata, Torrance, CA (US); Patricia S. Pao, New York, NY (US)

(73) Assignee: Restorsea, LLC, New York, NY (US)

( * ) Notice: Subject to any disclaimer, the term of this patent is extended or adjusted under 35 U.S.C. 154(b) by 0 days.

(21) Appl. No.: 14/571,087

(22) Filed: Dec. 15, 2014

(65) Prior Publication Data

US 2015/0165002 A1    Jun. 18, 2015

Related U.S. Application Data

(60) Provisional application No. 61/915,988, filed on Dec. 13, 2013.

(51) Int. Cl.

| | | |
|---|---|---|
| A61K 38/48 | (2006.01) | |
| A61K 31/7048 | (2006.01) | |
| B05B 11/00 | (2006.01) | |
| A61K 45/06 | (2006.01) | |
| A61K 36/258 | (2006.01) | |
| A61K 38/43 | (2006.01) | |
| A61K 9/00 | (2006.01) | |
| A61K 8/00 | (2006.01) | |
| A61K 36/03 | (2006.01) | |
| A61K 36/48 | (2006.01) | |

(52) U.S. Cl.
CPC .............. *A61K 38/4886* (2013.01); *A61K 8/00* (2013.01); *A61K 9/0014* (2013.01); *A61K 31/7048* (2013.01); *A61K 36/03* (2013.01); *A61K 36/258* (2013.01); *A61K 36/48* (2013.01); *A61K 45/06* (2013.01); *B05B 11/30* (2013.01); *C12Y 304/24066* (2013.01)

(58) Field of Classification Search
None
See application file for complete search history.

(56) References Cited

U.S. PATENT DOCUMENTS

| | | |
|---|---|---|
| 5,510,120 A | 4/1996 | Jones et al. |
| 5,587,168 A | 12/1996 | Vanonou |
| 6,019,991 A | 2/2000 | Tanaka et al. |
| 6,346,245 B1 | 2/2002 | Walther et al. |
| 6,376,557 B1 | 4/2002 | Zaveri |
| 6,416,769 B1 | 7/2002 | Vromen |
| 6,551,606 B1 | 4/2003 | Golz-Berner et al. |
| 6,582,710 B2 | 6/2003 | Deckers et al. |
| 6,592,866 B2 | 7/2003 | Walther et al. |
| 6,599,513 B2 | 7/2003 | Deckers et al. |
| 6,716,450 B1 | 4/2004 | Yin et al. |
| 6,846,485 B2 | 1/2005 | Bjarnason |
| 7,094,415 B2 | 8/2006 | Marenick |
| 7,829,081 B2 | 11/2010 | Bookbinder et al. |
| 8,075,920 B2 | 12/2011 | Gammelsaeter et al. |
| 8,460,713 B2 | 6/2013 | Gammelsaeter et al. |
| 8,557,295 B2 | 10/2013 | Gammelsaeter et al. |
| 8,992,996 B2 | 3/2015 | Alabata et al. |
| 2002/0064857 A1 | 5/2002 | Walther et al. |
| 2003/0115686 A1 | 6/2003 | Grey |
| 2004/0151684 A1 | 8/2004 | Mori et al. |
| 2005/0075265 A1 | 4/2005 | De Salvert et al. |
| 2005/0129739 A1 | 6/2005 | Kohn et al. |
| 2005/0163872 A1 | 7/2005 | Khare |
| 2006/0018867 A1* | 1/2006 | Kawasaki et al. ......... 424/70.122 |
| 2006/0073211 A1 | 4/2006 | Marenick et al. |
| 2006/0105005 A1 | 5/2006 | Marenick et al. |
| 2006/0257386 A1 | 11/2006 | Zimmerman et al. |
| 2006/0289834 A1 | 12/2006 | Doisaki et al. |
| 2007/0074298 A1 | 3/2007 | Kishimoto et al. |
| 2007/0243132 A1 | 10/2007 | Russell et al. |
| 2008/0161229 A1 | 7/2008 | Matsunaga et al. |
| 2009/0035240 A1 | 2/2009 | Maes et al. |
| 2009/0274770 A1 | 11/2009 | Gammelsaeter et al. |
| 2010/0260695 A1 | 10/2010 | Burke-Colvin et al. |
| 2011/0020302 A1 | 1/2011 | Banov et al. |
| 2011/0027327 A1 | 2/2011 | Albrecht |
| 2011/0097293 A1 | 4/2011 | Grey et al. |
| 2011/0108049 A1 | 5/2011 | Miyazaki et al. |
| 2011/0280882 A1 | 11/2011 | Walther et al. |
| 2012/0082695 A1 | 4/2012 | Asam |

(Continued)

FOREIGN PATENT DOCUMENTS

| | | |
|---|---|---|
| AU | 2007200216 | 8/2007 |
| EP | 139468 | 1/1990 |

(Continued)

OTHER PUBLICATIONS

MedicOnline, Z Skin Repair Scalp Tincture 75ml, Accessed May 16, 2015, Online at: translate.google.com/translate?hl=en&sl=sv& u=http://www.mediconline.se/z-skin-repair-scalp-tincture-75ml-p-321-c-110.aspx&prev=search.*

Truth in Aging, Glucosyl Hesperidin, Mar. 9, 2009, Available online on or before Oct. 24, 2012 as evidenced by Internet Archive Wayback machine, at: www.truthinaging.com/ingredients/glucosyl-hesperidin.*

Warner et al., "Water Disrupts Stratum Corneum Lipid Lamellae; Damage is Similar to Surfactants," J Invest Dermatol., Dec. 1999;113:960-966.

Yasumasu et al., "Isolation and Some Properties of Low Choriolytic Enzyme (LCE), a Component of the Hatching Enzyme of the Teleost, Oryzias latipes," J Biochem., Feb. 1989;105:212-218.

(Continued)

*Primary Examiner* — Karen Cochrane Carlson
*Assistant Examiner* — Jennifer M. H. Tichy
(74) *Attorney, Agent, or Firm* — Fish & Richardson P.C.

(57) ABSTRACT

A formulation or a pair of formulations is provided that includes a hair retention-promoting substance and an enzyme that is a peptidase or a lipase and that, when applied to a human scalp, has exfoliating activity. The substance and the enzyme are present in an aqueous carrier having a pH that maintains activity of the enzyme. A process of promoting hair retention on the scalp of a subject is provided in which a hair retention-promoting substance is topically administered to the scalp after, or in concert with, exfoliation of the scalp with an enzyme.

25 Claims, No Drawings

(56) References Cited

U.S. PATENT DOCUMENTS

| | | | |
|---|---|---|---|
| 2012/0107412 A1* | 5/2012 | Gammelsaeter et al. | 424/582 |
| 2012/0123442 A1 | 5/2012 | Larsen et al. | |
| 2012/0288478 A1 | 11/2012 | Florence et al. | |
| 2012/0309689 A1 | 12/2012 | Leren et al. | |
| 2013/0028947 A1 | 1/2013 | Albrecht | |
| 2013/0129742 A1 | 5/2013 | Walther et al. | |
| 2013/0202581 A1 | 8/2013 | Fallon et al. | |
| 2013/0261063 A1 | 10/2013 | Gammelsaeter et al. | |
| 2013/0336948 A1 | 12/2013 | Alabata et al. | |
| 2014/0037752 A1 | 2/2014 | Gammelsaeter et al. | |
| 2014/0072547 A1 | 3/2014 | Alabata et al. | |
| 2014/0220088 A1 | 8/2014 | Walther et al. | |
| 2014/0275289 A1 | 9/2014 | Weisman et al. | |

FOREIGN PATENT DOCUMENTS

| | | | |
|---|---|---|---|
| EP | 1089704 B1 | | 2/2004 |
| EP | 1397200 B1 | | 4/2007 |
| JP | 2009207473 | | 9/2009 |
| JP | 201065048 | | 3/2010 |
| KR | 1020050083960 | | 8/2005 |
| KR | 20080059066 | | 6/2008 |
| WO | 9929836 | | 6/1999 |
| WO | WO0007627 | | 2/2000 |
| WO | 2010042399 | | 4/2010 |
| WO | 2010049688 | | 5/2010 |
| WO | 2011006508 | | 1/2011 |
| WO | WO2011006434 | | 1/2011 |
| WO | 2011064384 | | 6/2011 |
| WO | 2011135059 | | 11/2011 |
| WO | 2012175742 | A2 | 12/2012 |
| WO | 2012175743 | A2 | 12/2012 |
| WO | 2013078259 | A2 | 5/2013 |
| WO | 2013112569 | | 8/2013 |
| WO | 2014091312 | | 6/2014 |
| WO | 2014094918 | | 6/2014 |
| WO | 2014096187 | | 6/2014 |

OTHER PUBLICATIONS

Aqua Bio Technology, Aquabeautine XL®—The Natural and Gentle Skin Refinisher [online], retrieved on Apr. 25, 2014. Retrieved from the Internet: http://www.aquabiotechnology.com/index.php?id=5.

Bumble and bumble Products, LLC, Concen-Straight Smoothing Treatment, Mar. 31, 2012, Bumbleandbumble.com.

Chantasart et al., "Structure Enhancement Relationship of Chemical Penetration Enhancers in Drug Transport across the Stratum Corneum," Pharmaceutics, Jan. 17, 2012;4:71-92. doi: 10.3390/pharmaceutics4010071.

Medic Online Sverige, Z Skin Repair, available on the Internet: http://www.mediconline.se/z-skin-repair-scalp-tincture-75ml-p-321-c-159.aspx, Accessed Feb. 21, 2014.

Perricone MD, Blue Plasma [online], retrieved on Apr. 25, 2014. Retrieved from the Internet: http://www.perriconemd.com/product/blue+plasma.do.

Restorsea LLC, The Restorsea 3-Step Regimen [online], retrieved on Apr. 25, 2014. Retrieved from the Internet: http://www.restorsea.com/info/Regimen_Offer.

Restorsea Revitalizing Eye Cream, 0.5oz—Bergdorf Goodman [online], retrieved on Apr. 25, 2014. Retrieved from the Internet: http://www.bergdorfgoodman.com/Restorsea-Revitalizing-Eye-Cream-0-5oz-restorsea/prod97540004_/p.prod?icid=&searchType=MAIN&rte=%252Fsearch.jsp%253FN%253D0%2526Ntt%253Drestorsea%2526_requestid%253D43404&eItemId=prod97540004&cmCat=search.

Z Skin Repair Intensive Cream Electi Medicals, <http://www.halsans.com/en/body-care/skin-hair-nail-products/z-skin-repair-intensive-cream/>; <http://nordicexpressions.org/z_skin_repair.htm>, Sep. 2014.

ZONA™ Extra Skin Repair [online], retrieved on Apr. 25, 2014. Retrieved from the Internet: http://www.amil.com.pl/?id=51&mod=& tpl=&_action=.

ZONA™ Shampoo [online], retrieved on Apr. 25, 2014. Retrieved from the Internet: http://www.amil.com.pl/?id=53&mod=&tpl=&_action=.

ZONA™ Sensitive [online], retrieved on Apr. 25, 2014. Retrieved from the Internet: http://www.amil.com.pl/?id=52&mod=&tpl=&_action=.

AA2G stabilised vitamin C from Hayashibara. Hayashibara International, Inc., Apr. 1, 2003.

Bai et al., "Toxicity of zinc oxide nanoparticles to zebrafish embryo: a physicochemical study of toxicity mechanism," J Nanopart Res., 2010;12:1645-1654.

Bedford, Robert F., NDA 19-617/S027—Diprivan (propofol) Injectable Emulsion Apr. 26, 1996.

Biotechmarine (R), "Kalpariane (R) ," www.labo-esthesante.fr/minexcell28/pdf/7726_2.pdf, Aug. 13, 2008.

Cho et al., "The Antioxidant Properties of Brown Seaweed (*Sargassum siliquastrum*) Extracts," J Med Food, 2007;10:479-485.

Cowan, M.M., "Plant Products as Antimicrobial Agents," Clinical Microbiology Reviews, Oct. 1999;12(4)564-582.

Coste, F., Multi-functional Marine Active Ingredient as a Gentle Alternative to AHAs, http://www.google.com/url?url=http://www.in-cosmetics.com/novadocuments/11186&rct=j&frm=1&q=&esrc=s&sa=U&ei=avsRVPLIMM6PyASAIILABg&ved=0CC0QFjAl&sig2=nytjK8ymfCWZGJGhNxrEdA&usg=AFQjCNGWxmhHbdcOMJ0pjVA1-xwC26FF0w, Apr. 2012, p. 9,10,25.

The Restorsea 3-Step Regimen, http://www.restorsea.com/info/Regimen_Offer#tabs, Jul. 1, 2014.

Franklin et al., "Comparative Toxicity of Nanoparticulate ZnO, Bulk ZnO, and ZnCl2 to a Freshwater Microalga (*Pseudokirchneriella subcapitata*): The Importance of Particle Solubility," Environ. Sci. Technol., 2007;41:8484-8490.

Hare (SA Pharmacists's Assistant (Summer 2007) p. 30).

Blue Plasma, http://www.perriconemd.com/product/blue+plasma.do, Oct. 7, 2012.

http://plants.usda.gov/core/profile?symbol=LOJA (accessed Oct. 31, 2013).

Karasakai et al., Determination of vitamin e (o-tocopherol) in canola oils by high performance liquid chromatography, Planta Medica, 2011;77:PA28.

"Omega-3,6, and 9 and How They Add Up," (http://www.uccs.edu/Documents/peakfood/hlthTopics/Omega-3_6_and_9_Fats.pdf).

LEX—Ground Breaking Natural Multifunctional Technology for Age Management and Improvement of Skin Appearance, http://www.regenics.no/filer/cosmetics.htm, Mar. 4, 2013.

Lonne, GK et al., "Composition Characterization and Clinical Efficacy Study of a Salmon Egg Extract," Int J Cosmet Sci., Oct. 2013;35(5):515-22.

Orsetti, Valeria, thesis: "Molecular Studies of Piscine Hatching Enzymes," http://tesi.cab.unipd.it/14043/1/Orsetti_Valeria.pdf, 2007.

Prospectus of Aqua Bio Technology ASA; Dec. 2007.

Screenshot of http://www.amil.com.pl/?id=25&mod=&tpl=&_action= (machine translation), Aug. 12, 2009.

Screenshot of http://www.apothekenbote.at/zona-sensitive-creme-75ml.html (machine translation), Jul. 2007.

Screenshot of http://www.mediconline.se/hudvard/problemhud/zona-byter-namn-till-z-skin-repair-c-160-1.aspx (machine translation), Sep. 30, 2011.

Screenshot of nordicexpressions.org/zona.htm ZSkinRepair Series1 .pdf Oct. 31, 2007 (The Z Skin Repair Series for problem Skin).

Screenshot of nordicexpressions.org/zona.htm ZSkinRepairSeries2.pdf Oct. 31, 2007 (Z Skin Repair and Zonase—a patented solution for problem skin).

Screenshot of nordicexpressions.org/zona.htm ZSkinRepairSeries3.pdf Oct. 31, 2007 (Z Skin Repair Extra Intensive Cream).

Screenshot of nordicexpressions.org/zona.htm ZSkinRepairSeries4.pdf Oct. 31, 2007 (Z Skin Repair Kids Sensitive Cream).

Screenshot of nordicexpressions.org/zona.htm ZSkinRepairSeries5.pdf Oct. 31, 2007 (Z Skin Repair Shampoo).

Screenshot of nordicexpressions.org/zona.htm ZSkinRepairSeries6.pdf Oct. 31, 2007 (Z Skin Repair Scalp Lotion Spray).

(56) References Cited

OTHER PUBLICATIONS

Screenshot of nordicexpressions.org/zona.htm ZSkinRepairSeries7.pdf Oct. 31, 2007 (Z Skin Repair Hand & Nail Cream).
Screenshot of nordicexpressions.org/zona.htm ZSkinRepairSeries8.pdf Oct. 31, 2007 (Z Skin Repair Lip Balm).
Screenshot of http://nordicexpressions.org/z_skin_repair.htm; Nov. 26, 2013.
Screenshot of shopping4net.se/HaelsokosWaard-hygien/Salvor/Zona-Sensitive.htm (machine translation) Nov. 27, 2007.
Wang et al., "Total phenolic compounds, radical scavenging and metal chelation of extracts from Icelandic seaweeds," Food Chemistry, 2009;116: 240-248.
Warner et al., "Release of Proteases from Larvae of the Brine Shrip Artemia Franciscana and Their Potential Role During the Molting Process," Comp Biochem Physiol B-Biochem. Mol. Biol. Feb. 1998;119(2):255-63.
International Search Report and Written Opinion for App. Ser. No. PCT/US2014/070126, mailed Mar. 31, 2015.
Restorsea Exfoliating Scalp Treatment product description [online], retrieved on Apr. 7, 2015. Retrieved from the Internet: http://www.restorsea.com/dp/B00JFHXEOS.
Aqua Bio Technology ASA, Aquabeautine XL brochure, 6 pages, dated Dec. 2011.
StyleBistro: Are Scalp Treatments the Next Big Thing in Haircare? (Apr. 30, 2014) [online], retrieved on Apr. 6, 2015. Retrieved from the Internet: http://www.stylebistro.com/Hair+Trend+Report/articles/28bV4YWOIVI/Scalp+Treatments+Next+Thing+Haircare.
Restorsea product brochure, Oct. 2014.
Restorsea product brochure, May 29, 2014.
Al-Edresi et al., "Formulation and stability of whitening VCO-in-water nano-cream," *Int J Pharm.*, 2009;373:174-178.
Alpha Glucosyl Hesperidin product brochure, 3 pages.
CAS Common Chemistry. Registry No. 111-01-3, http://www.commonchemistry.org/ChemicalDetail.aspx?ref=111-01-3, accessed on Jun. 19, 2015.
Clarins Intensive Serum Bi-Phase, Mintel, Sep. 2009. Database GNPD [online], XP-002742003, Database accession No. 1172601.
Cosmetic Ingredient Analysis: Whitening Agents, http://www.brunswicklabs.com/whitening-agents, available on May 23, 2010; accessed on Jun. 19, 2015.

"Z Skin Repair Scalp Tincture 75 ml" (Google Translate from Swedish to English), Retrieved from the Internet on Aug. 15, 2015: https://translate.google.com/translate?hl=en&sl=sv&u=http://www.mabrapostorder.se/se/z-skin-repair-scalp-tincture-75-ml.php&prev=search, 1 page.
International Search Report and Written Opinion for App. Ser. No. PCT/US2015/029853, mailed Jul. 29, 2015.
Packman and Gans, Topical moisturizers: quantification of their effect on superficial facial lines, *J. Soc. Cosmet. Chem.*, 29, 79-90 (1978).
Pillai et al., "1,2-Alkanediols for Cosmetic Preservation," Cosmetics & Toiletries (Oct. 1, 2008) [online] [retrieved on Aug. 19, 2015]. Retrieved from the Internet: http://www.cosmeticsandtoiletries.com/formulating/function/preservatives/premium-12-alkanediols-for-cosmetic-preservation-228198361.html, 7 pages.
Restorsea 24kt Liquid Gold Face Oil product description and ingredients [online], [retrieved on May 4, 2015]. Retrieved from the Internet: http://www.restorsea.com/dp/B00LU20LO2, 6 pages.
Restorsea Rolls Out 24-Karat Gold Face Oil (Oct. 2, 2014) [online], [retrieved on Apr. 6, 2015]. Retrieved from the Internet: http://www.happi.com/issues/2014-10-01/view_breaking-news/restorsea-rolls-out-24-karat-gold-face-oil/, 6 pages.
Schaefer, K., "Broad-spectrum Alternative to Caprylyl Glycol Preservative Blends," Cosmetics & Toiletries (Jan. 19, 2012) [online] [retrieved on Aug. 19, 2015]. Retrieved from the Internet: http://www.cosmeticsandtoiletries.com/formulating/function/preservatives/137670898.html , 2 pages.
Symrise, Hydrolite-5 active ingredients, 2 pages.
Symrise, Hydrolite® 6 benefits, 1 page.
Symrise Sensory Ingredients, Sensory News, Oct. 2005, 2 pages.
Symrise, Symdiol 68: Synergistic Diol Blend product brochure, 26 pages.
Supplementary European Search Report for App. Ser. No. EP 13 74 0793, dated May 8, 2015, 3 pages.
U.S. Food & Drug Administration, Appendix—Chelation potential of disodium EDTA [online] [retrieved on Aug. 19, 2015]. Retrieved from the Internet: http://www.fda.gov/downloads/Drugs/GuidanceComplianceRegulatoryInformation/ucm117682.pdf, 2 pages.

* cited by examiner

EXFOLIATIVE HAIR RETENTION-PROMOTING FORMULATION

RELATED APPLICATIONS

This application claims priority benefit of U.S. Provisional Application Ser. No. 61/915,988, filed 13 Dec. 2013, the contents of which are hereby incorporated by reference.

FIELD OF THE INVENTION

The present invention in general relates to a formulation for promoting hair retention, and in particular to a formulation and process for the use thereof to provide a more efficient usage of follicle health-promoting agents.

BACKGROUND OF THE INVENTION

Numerous plant extracts and pharmaceuticals have been identified as promoting overall hair follicle health and even promoting hair retention during a follicle rest period. Unfortunately, some users of such products are dissatisfied by the results obtained with such conventional products. Dissatisfaction may occur even in instances when the formulation achieves good results in vitro as well as under controlled clinical studies.

There has been considerable research effort expended to understand the biochemistry of hair retention and to develop compounds promoting hair retention. Unfortunately, there have not been commensurate advances in the development of delivery systems for the transport of topically administered compounds into contact with target cells within the hair follicle in general, and in particular, to the follicle basal cells.

The anatomy of the hair follicle includes the outermost layer of corneum stratum that has dead and dying dermal cells that form a constriction around the protruding hair shaft. Sebaceous secretions also coat the hair shaft and render the path a topical hair retention agent must take to reach the follicle physically blocked and hydrophobic. Prior art attempts to administer active agents to the follicle basal cells using emulsions have met with limited success owing to the user displeasure with the application of this type of vehicle to the scalp. In addition, emulsions are known to change topical delivery kinetics of active agents (S. Y. E. Hou et al. "Phase volume and partitioning effects on drug delivery from topical emulsions"; International Journal of Pharmaceutics, 66 (1990) 79-85).

Thus, there exists a need for an exfoliating, hair retention-promoting formulation to more efficiently deliver hair retention-promoting agents to the hair follicle. There also exists a need for such a formulation that is an aqueous solution or suspension.

SUMMARY OF THE INVENTION

A formulation is provided that includes a hair retention-promoting substance and an enzyme that is a peptidase or lipase, where the enzyme is active in exfoliating a human scalp. The substance and the enzyme are present in an aqueous carrier having a pH that maintains activity of the enzyme.

A process is provided for enzymatically exfoliating the scalp of a subject for the purpose of promoting hair retention on the subject's scalp. A hair retention-promoting substance is topically administered to the scalp of the subject after, or in concert with, the exfoliation of the scalp. A kit is also provided for performing the process with a first exfoliating phase and a second hair retention-promoting phase, where the two formulations are packaged separately, or alternatively the kit may contain a combined formulation containing both the exfoliating enzyme and the hair retention-promoting substance. The kit also contains instructions for using the components to achieve the desired hair retention.

DESCRIPTION OF THE INVENTION

The present invention has utility in promoting hair retention. Whether scalp exfoliation precedes administration of a hair retention-promoting substance, or the two steps are carried out together, e.g., by administration in a formulation containing both the exfoliating agent and the hair retention-promoting substance, enhanced hair retention promotion is accomplished, as compared to administration of the hair retention-promoting substance without exfoliation.

Without intending to be bound to a particular theory, exfoliation associated with mechanical abrasion or chemical peeling causes inflammation to the scalp that appears to counteract many of the benefits associated with inventive exfoliation. Chemical peel exfoliation is most often associated with the usage of compounds illustratively including glycolic acid and retinoic acid. Instead, the present invention relies on an enzymatic scalp exfoliant that allows hair retention promoting substance to penetrate around the hair fiber to the papilla. Limiting of inflammation associated with exfoliation appears to promote hair retention promoting substance efficacy.

It is to be understood that, in instances where a range of values is provided herein, the range is intended to encompass not only the end point values of the range, but also individual intermediate values and intermediate ranges within the range By way of example, a recited range of from 1 to 4 is intended to include not only 1-4, but also 1, 2, 3, 4, 1-2, 1-3, 2-4, and 3-4.

According to the present invention, an active enzyme is provided that has an exfoliating effect on human corneum stratum. The active enzyme is in an aqueous carrier that maintains activity of the enzyme during storage. Peptidase enzymes, lipase enzymes and combinations thereof are active enzymes in an inventive formulation and illustratively include trypsin, bromelain, papain, proteins active in natural degrading of egg zona (synonymously referred to herein as egg hatching active proteins), and combinations thereof. Specific egg hatching active proteins operative herein include fish spawn proteins such as zonase (a serine protease) and choriolysin (a zinc protease). It is appreciated that the quantity of active protein present depends on factors illustratively including aqueous carrier pH, enzyme specificity, enzyme activity, carrier viscosity, and enzyme half-life.

As used herein, a peptidase is defined as an enzyme that catalyzes hydrolysis of a peptide bond that links two amino acids together in a polypeptide chain. The term "peptidase" is used herein synonymously with "protease" and "proteinase".

A fish spawn protein isolate, for example, includes a zonase, a leukolectin, a choriolysin, or a combination thereof, and has the properties detailed in U.S. Pat. No. 6,346,245, col. 4, line 15-col. 5, line 8; U.S. 2009/0274770 A1 [0321]-[0326] and U.S. 2011/0280882 [0157]-[0194]; crude extracts containing such proteins; and combinations thereof. Exemplary sources of fish spawn for protein isolation include roes from sturgeon, salmon, whitefish, vendace, cod, capelin, and burbot. It is appreciated that other sources of egg proteins operative herein include amphibian egg cases such as those of tadpoles and salamanders; reptilian egg cases, and fowl egg cases. Typically, an egg- or, with particularity, fish spawn protein-isolate containing at least one of the above recited proteins constitutes from 0.1 to 10% total weight of an inventive formulation, with 0.00001 to 10 percent of the extract being active protein. To give just one example, a given active protein may constitute $1\times10^{-8}$ to $1\times10^{-5}$ total weight percent of the formulation (i.e., 0.00001 to 10 percent of the extract is the protein, and the extract is 0.1% total weight of the formulation). It is appreciated that the amount of protein present in an inventive cosmetic depends on factors illustratively including miscibility with other components.

The active enzyme in the aqueous carrier is readily applied to the scalp in certain inventive embodiments as a first treatment step. The enzyme produces a non-inflammatory exfoliation in and around the hair follicle. In other inventive embodiments, the active enzyme is part of a single formulation that also contains the hair retention-promoting substance.

Typical loadings of active enzyme range from 0.000001 to 1,000 enzyme units (U) per liter, where an enzyme unit corresponds to one micromole of substrate converted per minute. For purposes of determining U, an in vitro assay can be carried out using an oligopeptide substrate that represents the target protein(s) of corneum stratum. In some embodiments, the oligopeptide is chromogenic, and cleavage thereof by the enzyme produces a detectable color change. While it is appreciated that aqueous carrier pH is readily tailored to modify peptidase enzymatic activity, typical aqueous carrier pH values range from 6 to 8 for many peptidase enzymes operative herein. Exemplary of peptidases active in this pH range are zonase and trypsin.

In some embodiments, an inventive formulation includes the peptidase enzyme and a hair retention-promoting substance combined in an aqueous carrier. It is appreciated that an inventive formulation containing both the active enzyme and the hair retention-promoting substance facilitates user compliance, as only a single formulation need be applied. In some embodiments, the formulation (or both formulations, when separate formulations are used) may conveniently be applied as a leave-in spray solution, which also facilitates user compliance.

Regardless of whether the present invention is practiced as an exfoliating enzymatic step and a separate hair retention-promoting substance step, or if these two steps are combined into one by using a single formulation containing both active ingredients, application to the scalp typically occurs on a regime of once a week, 2-6 days per week, once daily, or even two or three times daily. It is appreciated that, when the two ingredients are applied in separate steps, the timing and frequency of the first can vary from the timing and frequency of the second. By way of example, upon effecting exfoliation with one or more applications of the enzyme, multiple doses of hair retention-promoting substance may be applied (e.g., once per day for multiple days) before the exfoliation step is repeated. It may be sufficient to do only occasional maintenance application of the enzymatic exfoliant.

As used herein, a hair retention-promoting substance is defined as a substance that promotes hair retention and is a purified organic compound, a natural product extract containing one or more such compounds, or a synthetic compound. The substance may be, for example, an inhibitor of prostaglandin-D2 or an inhibitor of dihydro-testosterone. It is appreciated that many natural product extracts, including some that contain polyphenols, have been shown to be effective in promoting hair retention. Specific hair retention-promoting substances operative herein illustratively include minoxidil, red ginseng extract, hesperidin extract, green pea shoot extracts, synthetic oligopeptides sold under the tradename SymPeptide™, and combinations thereof. It is appreciated that hair retention-promoting substances are typically used in an inventive formulation from 0.001 to 1 total weight percent, but can be up to 10 total weight percent, e.g., where the extract contains a relatively low concentration of active agent. An inventive formulation is readily formulated as a water based solution or as an emulsion containing an aqueous carrier phase for the enzymes. It is appreciated that some hair retention-promoting substances are lipophilic, while others are hydrophilic. Lipophilic hair retention-promoting substances are readily formulated as a two-phase formulation with a solvent appropriate for dissolution or suspension of the hair retention-promoting substance. The solvents illustratively include skin-compatible alcohols, ketones, esters, aldehydes, ethers, alkanes, alkenes, alkylated sulfoxides; cyclics of any of the aforementioned; fluorinated analogs of any of the aforementioned; and combinations thereof. Specific solvents for certain hair retention-promoting substances (either single compound or extract) illustratively include water, ethanol, isopropanol, acetone, glycols, alkoxylated glycols, diethyl ether, pentane, hexane, dimethyl sulfoxide, and combinations thereof. In some embodiments, lipophilic hair retention-promoting substances are present in an oil phase of an oil-in-water or water-in-oil emulsion.

In still other inventive embodiments, an anti-inflammatory agent is included in an enzyme and hair retention-promoting substance combined formulation, or in one or both parts of a two-formulation embodiment (one formulation containing the active enzyme and the other formulation containing the hair retention-promoting substance. Anti-inflammatory agents operative herein illustratively include steroidal anti-inflammatory agents; non-steroidal anti-inflammatory agents; extracts of plants such as turmeric, oregano, garlic, green tea, blueberries, neem, holy basil oil, licorice, ashwaganda, raspberry leaf, St. John's Wort, chamomile, and ginger; omega fatty acids; alpha-linolenic acid; and combinations thereof.

In still other inventive embodiments, an antioxidant may be included in a mixed enzyme and hair retention-promoting formulation, or in one or both parts of a two-formulation embodiment. Antioxidants operative herein illustratively include alpha lipoic acid, beta-glucan, coenzyme Q10, grape seed extract, oat extract, chamolime, green tea, soybean sterols, superoxide dismutase, vitamin C (e.g., in the form of ascorbyl palmitate, magnesium ascorbyl palmitate, or ascorbic acid 2-gluconate), and vitamin E (e.g., alpha tocopherol or a tocotrienol), and combinations thereof. It is appreciated that a number of anti-inflammatory agents possess antioxidant properties. The formulations of the invention that include such an anti-inflammatory agent may also include a separate antioxidant compound.

In still other embodiments of the present invention, a formulation or a single component thereof is provided that is essentially free of synthetic compounds. In still other embodiments, a formulation or a single part thereof is provided that is certified organic.

In certain embodiments, a single, mixed formulation is provided containing both the peptidase enzyme and the hair retention-promoting substance in an aqueous solution that is suited for use as leave-in scalp spray or wash. When the aqueous carrier evaporates, it leaves the active enzyme and substance in contact with the scalp.

To maintain peptidase or lipase enzyme activity, a process of formulation includes the buffering of any constituent phase containing the enzyme(s) to a pH of between 5 and 8 prior to introduction of enzyme to that phase. Buffering is commonly practiced in the field and includes the addition of an acid, a base, a salt of an acid, or a combination thereof to equilibrate an aqueous solution or aqueous phase of an emulsion to a desired pH. It is appreciated that pH measurement is routine.

pH may be measured quantitatively via volumetric titration or with potentiometric electrodes such as those commercially available from Thermo Fisher Scientific (Waltham Mass., USA), or qualitatively with litmus paper kits.

Biocides are present in some inventive embodiments. A biocide helps maintain product quality by inhibiting growth of microorganisms introduced during formulation of the product or during use thereof, particularly when the product is packaged in multiple-use packaging, so is exposed to continual microbial seeding from the environment or the user. An inventive formulation may optionally include a broad spectrum biocide and/or a combination of biocides. A broad spectrum biocide is defined herein as having activity against Gram positive bacteria, Gram negative bacteria, and fungi associated with a healthy human subject. Biocides operative herein illustratively include benzoic acid, parabens, salicylic acid, carbolic acid, sorbic acid, alkyl p-hydroxybenzoates, p-chlorometacresol, hexachlorophene, benzalkonium chloride, chlorohexidine chloride, trichlorocarbanilide, phenoxyethanol, acylsarcosines, glutathione, malic acid, tartaric acid, ascorbic acid, ascorbic acid glucoside, ascorbates, essential plant oils, mutacin proteins, and combinations thereof. In certain embodiments of the present invention, only naturally-derived biocides—i.e., biocides found in nature or extracted from a natural source—are present. Naturally derived biocides illustratively include fermentation filtrates such as those of *Lactobacillus, Streptococcus mutans*, and *Leuconostoc*; bisabolol; eucalyptol; thymol; inositol; saponins; and natural extract of plants, such as Japanese honeysuckle (*Lonicera japonica*), yangti (*Rumex japonicus*), kushen (*Sophora flavescens*), candock, wild oregano, orange, sage, manifoil, common mallow, chuanxiong (*Cnidii officinale* Makino), Japanese green gentian (*Swertia japonica* Makino), bisabolol, thyme, danguii (*Angelica sinensis*), orange peel, birch, field horsetail, dishcloth gourd, horse chestnut tree, creeping saxifrage (*Saxifrage stolonifera*), arnica, lily, mugwort, peony, aloe, *gardenia*, as well as those detailed in M. M. Cowan, Clinical Microbiology Reviews, 12(4) October 1999, p. 564-582; or combinations thereof. Such extracts are obtained by procedures detailed in Clinical Microbiology Reviews, 12(4) October 1999, pages 573-574, often using a hydrophilic organic solvent such as a $C_1$-$C_8$ alcohol, polyhydric alcohols, water, and aqueous alcohols. In specific embodiments, Japanese honeysuckle, phloretin (derived from apples), and/or galangin (e.g., from *Alpinia officinarum* or *Helichrysum aureonitens*) are used as naturally derived biocides, each alone or in combination. It is appreciated that in addition to biocide properties, a natural extract often imparts a fragrance to an inventive formulation or phase thereof. In specific embodiments, a biocide may be present in the formulation(s) from 0.1 to 5 total weight percent. It is appreciated that quantities of biocides beyond 5 total weight percent may be included as desired. It is further appreciated that in some instances the inclusion of transition metal ions is used to reduce enzymatic activity of microbes.

In still other embodiments of the present invention, the formulation containing the exfoliative enzyme may be provided in a sterile form. Sterilization may be accomplished by any standard means that does not denature or degrade the enzyme. While heat or radiation may be possible, more typically size exclusion sterilization (i.e., filtration) will be used to remove contaminating bacteria and in some cases viruses from a solution containing the enzyme, or from the final formulation itself. It is appreciated that single-use packages are best suited for maintaining sterility of the sterilized formulation, as airborne microbes or microbes associated with the subject tend to infiltrate an opened package.

In some embodiments, the formulation(s) are packaged in a container having a pump atomizer. In other embodiments, the container is a pressurized spray can, a squeeze bottle or squeeze tube, a bottle with an applicator (separate or attached), a single-use vial, or any other appropriately configured container. The container may be formed of plastic, glass, or metal.

One part and two-part versions of the present invention are illustrated in exemplary form in Tables 1 and 2, respectively.

TABLE 1

Typical ranges of ingredients in a one-part formulation, where the percentages are total weight percent.

| | |
|---|---|
| Deionized water | Remainder |
| Exfoliating enzyme solution | 0.001 to 10% |
| Hair retention-promoting substance | 0.001 to 10% |
| Antioxidant | 0 to 5% |
| Anti-inflammatory agent | 0 to 5% |
| pH adjuster/buffer | 0 to 5% |
| Biocide | 0.1 to 10% |
| Fragrance | 0 to 5% |
| Citric acid | 0 to 1% |

TABLE 2

Typical ranges of ingredients in each of the two parts of a dual-formulation embodiment, where the specified percentages denote total weight percent.

| | |
|---|---|
| Part 1 - Exfoliator | |
| Deionized water | Remainder |
| Exfoliating enzyme solution | 0.001 to 10% |
| Antioxidant | 0 to 5% |
| Anti-inflammatory agent | 0 to 5% |
| pH adjuster/buffer | 0 to 5% |
| Biocide | 0.1 to 10% |
| Fragrance | 0 to 5% |
| Vitamin(s) | 0 to 1% |
| Part 2 - Hair retention promoter | |
| Deionized water/solvent | Remainder |
| Hair retention-promoting substance | 0.001 to 10% |
| Antioxidant | 0 to 5% |
| Anti-inflammatory agent | 0 to 5% |
| pH adjuster/buffer | 0 to 5% |
| Biocide | 0.1 to 10% |
| Fragrance | 0 to 5% |
| Vitamin(s) | 0 to 1% |

It has been found that, as the active enzyme is prone to degradation through exposure to heat and mechanical agitation, the manner in which the formulation containing the enzyme is prepared is important to maintaining enzymatic activity. For example, one can add the enzyme late in the formulation process, or one can minimize these sources of energy when the enzyme is present, or both.

In some embodiments, the inventive formulation is in the form of an emulsion. Without intending to be bound to a particular theory, an emulsion is well suited to wet the hair cortex, which tends to be lipophilic owing to secretion from sebaceous glands surrounding the hair follicle.

The minority phase components of an oil-in-water emulsion illustratively include oils, waxes, esters, ethers, butters, glycerides, or combinations thereof. The majority phase components of an oil-in-water emulsion may include, besides water: aqueous salts, humectants, and various water soluble materials as detailed above. An emulsifier for such a system may be selected from ionic surfactants, non-ionic surfactants and also including lecithin, liposomes, and oleosomes. Other non-essential additives are readily provided that include viscosity modifiers, emulsion stabilizers, fragrances, and the like. In specific embodiments, the oil-in-water emulsion has a pH value of 5 to 8. If certain embodiments, the oil-in-water emulsion has a pH value of 6 to 7, e.g., 6.5 to 6.8. It is appreciated that including an enzyme in an aqueous segment of a water-in-oil emulsion serves to stabilize the enzyme against storage degradation.

The water-in-oil emulsion or a water-in-silicone emulsion varies the relative quantities of minority and majority phase components and preferably relies on non-ionic surfactants and silicone derivatives as emulsifiers. Viscosity modifiers and/or emulsion stabilizers illustratively include water soluble salts, gums, waxes, and combinations thereof. In specific embodiments, the inner phase has a pH of 4 to 8. It is appreciated that various vitamins such as vitamin B complexes, vitamin E, vitamin K, ascorbic acid derivatives such as ascorbic acid glucosides, E-O-alkyl ascorbic acid, and ascorbate phosphates are readily provided in one or both of the aforementioned emulsion phases or provided as a separate third phase. The vitamin(s) may be in addition to the antioxidant and/or anti-inflammatory ingredients described above.

An inventive emulsion formulation is readily formed by combining premixed phases as detailed above or alternatively all such components are intermixed in sequence conventional to the art as a unified mixture-provided that, in a formulation containing active enzyme, care is taken not to subject the enzyme to excess heat or shear during the mixing process (if the enzyme is sensitive to same).

It should be appreciated that other conventional base formulations are readily adjusted as detailed herein to stabilize the active exfoliative enzyme. A variety of conventional base formulations are provided in E. W. Flick, "Cosmetic and Toiletry Formulations", 2$^{nd}$ Ed., Vol. 8; 2001, Noyes Publications, Norwich, N.Y., USA (ISBN 0-1855-1454-9).

A process of stimulating hair retention on a scalp is also provided. This process includes enzymatically exfoliating the scalp of a subject. In operation, the liquid formulation (solution, emulsion, or suspension) is applied to the subject's scalp and hair roots. This can be done by squirting or dabbing the formulation onto the target area, or by forming a mist with a propellant-based pressurized aerosol spray can or a manual spray pump equipped with a conventional atomizer nozzle, and directing the mist at the target area. Between 0.1 and 5 milliliters of liquid are sufficient to form a mist on the hair and underlying scalp, but the amount needed to achieve the hair retention effect will depend on factors that include the concentration of the enzyme, the concentration of the hair retention-promoting active agent, and the viscosity of the formulation. The application of the exfoliative enzyme and the application of the hair retention-promoting substance are readily performed as separate steps. Alternatively, one can apply them simultaneously, e.g., using a single formulation that includes both the peptidase enzyme and the hair retention-promoting substance. In instances where the two active agents are applied using separate formulations, it is appreciated that the two formulations can be similar or can be very different. For example, the enzyme will generally be formulated in an aqueous solution or an emulsion with an aqueous phase containing the enzyme. In contrast, the hair retention-promoting substance may be either hydrophilic or lipophilic and so may require a type of formulation different from that used for the enzyme.

In some usage regimens employing dual formulations, the first formulation (containing the active enzyme) is used routinely (e.g., daily) for the first several weeks along with regular application (e.g., daily or twice daily) of the second (hair retention-promoting) formulation; after a degree of exfoliation has been achieved, the first formulation is applied less frequently, for example, only every two or three days, while the frequency of applying the second formulation is maintained. Hair retention improvement is typically noted in two to three months.

The present invention is further illustrated with reference to the following non-limiting examples.

EXAMPLE 1

A process for forming a revitalizing scalp treatment in five steps in an aqueous solution of deionized water is provided. In step A, citric acid, sodium citrate, and a glucoside of ascorbic acid are added in that order to the deionized water in a main vessel, with each ingredient mixed with the water until blended prior to adding the next ingredient. In step B, sodium hydroxide (NaOH) (20%) is added to adjust the pH of the first mixture in the main vessel to between 6.5 to 6.8. In step C, glucosyl hesperidin and red ginseng extract (40% water, 60% butylene glycol and 0.2% *Panax Ginseng* Root Extract by weight), are added to the main vessel and mixed in until all solids dissolve and are uniformly blended. In step D, 1,2-hexanediol, pentylene glycol, and a brown algae extract in caprilic/capric triglyceride solvent (the extract containing, in milligrams per 100 grams of solvated extract: palmitic acid 28.2, palmitoleic acid 12.4, stearic acid 6.8, oleic acid 14.7, linoleic acid—(Omega 6) 7.2, a linolenic acid 9.7, omega 3 fatty acids 26.3, cholesterol 47.2, campesterol 45.9, stigmasterol 57.5, and sitosterol 142.8) are premixed in a separate vessel, and then added to the main vessel and mixed until blended. In step E, a salmon egg hatching enzyme solution containing leukolectin(s) or other lectins, choriolysin(s), and zonase (leukolectin content of 0.00068 wt. %, zonase content of 0.00034 wt. %, choriolysin content of 0.0000136 wt. %) is added to the main vessel and mixed until blended, forming the final formulation. Table 3 lists the aforementioned ingredients, where percentages are total weight percent.

TABLE 3

Exemplary inventive hair retention formulation.

| | |
|---|---|
| Deionized water | Remainder |
| Citric acid | 0.015% |
| Sodium citrate | 0.150% |
| Ascorbic acid glucoside | 0.001% |
| Sodium hydroxide (20%) | 0.027% |
| Glucosyl hesperidin | 1.000% |
| Red ginseng extract | 3.000% |
| 1,2-hexanediol | 1.000% |
| pentylene glycol | 5.000% |
| Brown algae extract | 0.001% |
| Salmon egg hatching protein solution | 1.000% |
| pH | 6.78 |
| Specific gravity | 1.005 |

EXAMPLE 2

The process of Example 1 is repeated with the addition of a vitamin complex containing in solution vitamins B3, B5, B6, C and E. The amount of the vitamin complex solution added is 2 percent of the final total weight, with a corresponding reduction in the amount of deionized water. The vitamins are present in the vitamin complex solution in amounts varying from 10 to 200 milligrams per 100 grams of vitamin complex solution.

EXAMPLE 3

A female subject suffering a daily hair loss of on average 52 hairs per day as measured by drain trap collection, commenced usage of the formulation of Example 1 on a daily basis with aerosol misting of the head with 1 milliliter of solution after routine shampoo and conditioner usage, followed by 5 minutes of dwell time prior to blow drying. After 8 weeks of daily use, daily hair loss was reduced to on average 4.6 hairs per day.

EXAMPLE 4

The method of Example 3 is repeated with the formulation of Example 2, resulting in a daily hair loss of on average 3.4 hairs per day.

EXAMPLE 5

The method of Example 1 is repeated, but with the omission of glucosyl hesperidin from the formulation. A reduction in daily hair loss is noted consistent with that of Example 3.

EXAMPLE 6

A clinical trial was conducted with the formulation of Example 1. Subjects were recruited with enrollment criteria that included: subject is female between the ages of 25 and 55 years; subject normally uses shampoo and conditioner, subject has hair length that is sufficient for evaluation, as determined by the cosmetologist; has Skin Type I-IV (ranging from white to moderately brown with skin reaction to sun within the range of "always burns" to "tans with ease"; subject sheds at least 20 hairs at the baseline evaluation; subject agrees to replace their usual hair shampoo and conditioner with the provided materials during the conditioning phase and for the duration of the study, subject agrees to apply the assigned scalp treatment once every other day for the duration of the study, subject agrees to protect the scalp from sun exposure; subject is in generally good health; and subject is dependable and able to follow directions as outlined in the protocol.

Enrolled subjects were instructed to apply the test material to the scalp every other day during the 24 week use period. Subjects were instructed to refrain from test material use and washing/conditioning the hair the morning of each visit. Subjects were also instructed to refrain from using any shampoos, conditioners, and scalp treatments (other than the materials provided), but were told they may continue styling their hair in the usual manner (i.e. blow dry, flat iron, curling iron) and may use their usual styling products.

After approximately 4, 8, 12, 16, 20, and 24 weeks of use, subjects returned to the laboratory with unwashed hair, having refrained from test material application on the morning of the visit. At each visit, MEDISCOPE® images of the scalp were obtained as described below. Visual grading of the hair was performed as described below. A cosmetologist washed and conditioned each subject's hair with Free & Clear™ Shampoo and Conditioner. Wet and dry hair collections were performed as described below.

FotoFinder MEDISCOPE® (FotoFinder Systems, Inc.) Testing Procedure

MEDISCOPE® combines the high resolution of digital photography with the direct capture features of a software archiving system and, in doing so, simplifies the photo-documentation process. Mediscope utilizes a Canon Powershot G10 (14.7 Mega Pixel). This camera takes photos in outstanding quality that can be seen immediately on-screen. The whole imaging process is completely controlled by the software. An overlay feature allows the baseline images to be overlaid onto the live preview images, thus ensuring almost exact repositioning at every visit. One digital image of the scalp (crown of the head) was collected at each visit. The hair of each subject was assessed by a cosmetologist using a modified Visual Analog Scale (VAS) at each visit. The cosmetologist selected a location on the 100 mm VAS scale that corresponds with the assessment of hair thickness/volume, in relation to the labeled vertical positions on the scale. The distance between the mark recorded and the left origin of the line was subsequently measured in millimeters, to allow for assignment of a numerical score for the extent of the evaluated parameter.

Hair Collections Procedure

At each visit, the hair was shampooed/conditioned by the cosmetologist at the laboratory using Free & Clear™ Shampoo and Conditioner. Subjects wore a drape (white for dark-haired subjects and black for light-haired subjects). The hair was detangled with a comb or pick, if necessary. The hair was divided into five sections. Each section was combed from root to end for five strokes, using a wide tooth comb. Any hair shed onto the drape or in the sink was collected and counted. The hair was then finger-blown dry. Once the hair was dry, the hair was divided into five sections. Each section was combed from root to end for five strokes, using a wide tooth comb. Any hair shed onto the drape was collected and counted.

Data Analysis

Total hair counts at each visit (wet and dry combined) and scores for clinical grading of hair appearance were listed for each subject and treatment and were analyzed statistically. Analysis of Variance with 2 factors (time as a fixed effect and subject as a random effect) was followed by a Dunnett's test applied to determine the differences between baseline and each post-treatment interval (Week 4, Week 8, Week 12, Week 16, Week 20, and Week 24). If the residuals of the Analysis of Variance were not distributed normally (Shapiro-Wilk test at the threshold of 1%), this analysis was carried on ranks.

Change from baseline was calculated at each post-treatment interval for the above mentioned parameters. Analysis of variance followed by Tukey multiple comparison post hoc test was applied to determine the differences in change from baseline between test formulation vs. placebo control.

The study results are provided in Tables 4 and 5. The values for subjects treated with the Example 1 formulation improved over time. Given the tolerance and low toxicity of a formulation of Example 1, usage in perpetuity is contemplated.

TABLE 4

Mean VAS Score for hair thickness/volume for at various time points
Mean VAS Score for Hair Thickness/Volume

| Treatment | Baseline | Week 4 | Week 8 | Week 12 | Week 16 | Week 20 | Week 24 |
|---|---|---|---|---|---|---|---|
| Example 1 | 51 | 54 | 54 | 55 | 54 | 57 | 58 |

TABLE 5

Mean total hair loss count at various time points.

Mean Total Hair Loss Count

| Treatment | Baseline | Week 4 | Week 8 | Week 12 | Week 16 | Week 20 | Week 24 |
|---|---|---|---|---|---|---|---|
| Example 1 | 67 | 56 | 47 | 38 | 29 | 28 | 27 |

Any patents or publications mentioned in this specification are herein incorporated by reference to the same extent as if each individual publication was specifically and individually indicated to be incorporated by reference.

The invention claimed is:

1. A method of promoting hair retention on a scalp of a subject, the method comprising:
   identifying a subject as being in need of increased hair retention;
   at a frequency of from once a week to two times daily for at least two months, applying to the subject's scalp a composition comprising ascorbic acid glucoside, one or more glycols, and a mixture of fish egg hatching proteins, wherein no other compound in the composition is a biocide; and
   leaving the composition to dry on the scalp after each application,
   wherein the composition is effective for promoting hair retention on the scalp of the subject.

2. The method of claim 1, wherein the composition is an aqueous solution comprising 1,2-hexanediol and pentylene glycol.

3. The method of claim 2, wherein the composition comprises a brown algae extract.

4. The method of claim 3, wherein the composition comprises glucosyl hesperidin.

5. A method of promoting hair retention on a scalp of a subject, the method comprising:
   identifying a subject as being in need of increased hair retention;
   at a frequency of from once a week to two times daily for at least two months, applying to the subject's scalp a composition comprising a mixture of fish egg hatching proteins, and leaving the composition to dry on the scalp after each application,
   wherein the fish egg hatching proteins together constitute $10^{-8}$ to 1% total weight of the composition, and the composition is effective at increasing hair retention on the subject's scalp.

6. The method of claim 5, wherein the composition is an aqueous composition comprising glycols and ascorbic acid glucoside.

7. The method of claim 6, wherein the glycols include pentylene glycol and 1,2-hexanediol.

8. The method of claim 6, wherein the composition contains no other biocide.

9. The method of claim 8, wherein the glycols include pentylene glycol and 1,2-hexanediol.

10. The method of claim 1, wherein the fish egg hatching proteins include a choriolysin.

11. The method of claim 5, wherein the fish egg hatching proteins include a choriolysin.

12. The method of claim 5, wherein the composition comprises glucosyl hesperidin.

13. The method of claim 1, wherein the composition is applied to the subject's scalp daily or every other day.

14. The method of claim 5, wherein the composition is applied to the subject's scalp daily or every other day.

15. The method of claim 1, wherein the composition is applied to the scalp by being sprayed from a container comprising a pump atomizer.

16. The method of claim 5, wherein the composition is applied to the scalp by being sprayed from a container comprising a pump atomizer.

17. The method of claim 1, wherein the composition comprises minoxidil, a polyphenol, a dihydrotestosterone inhibitor, or a green pea shoot extract.

18. The method of claim 5, wherein the composition comprises minoxidil, a polyphenol, a dihydrotestosterone inhibitor, or a green pea shoot extract.

19. The method of claim 5, wherein the composition comprises a brown algae extract.

20. A method of promoting hair retention on a scalp of a subject, the method comprising:
   identifying a subject as being in need of increased hair retention;
   at a frequency of from once a week to two times daily for at least two months, applying to the subject's scalp a composition comprising zonase, choriolysin, and one or more glycols; and
   leaving the composition to dry on the scalp after each application,
   wherein the composition is effective for promoting hair retention on the scalp of the subject.

21. The method of claim 20, wherein the composition comprises a brown algae extract.

22. The method of claim 20, wherein the composition is an aqueous solution and comprises citric acid, sodium citrate, ascorbic acid glucoside, glucosyl hesperidin, red ginseng extract, 1,2-hexanediol, pentylene glycol, and a brown algae extract.

23. A method of promoting hair retention on a scalp of a subject, the method comprising:
   identifying a subject as being in need of increased hair retention;
   at a frequency of from once a week to two times daily for at least two months, applying to the subject's scalp a composition consisting essentially of
      water,
      buffer,
      pH adjuster,
      ascorbic acid glucoside,
      glucosyl hesperidin,
      red ginseng extract,
      brown algae extract,
      glycols, and
      a fish spawn protein isolate from hatching salmon eggs; and
   leaving the composition to dry on the scalp after each application,
   wherein the composition is effective for promoting hair retention on the scalp of the subject.

24. The method of claim 23, wherein the fish spawn protein isolate comprises a zonase, a leukolectin, and a choriolysin.

25. The method of claim 23, wherein the buffer is a citric acid/citrate buffer and the pH adjuster is sodium hydroxide.

* * * * *